(12) United States Patent  (10) Patent No.: US 8,093,433 B2
Yoshii  (45) Date of Patent: Jan. 10, 2012

(54) PROCESS FOR PRODUCING ALKYLBENZENE HYDROPEROXIDE

(75) Inventor: Masayuki Yoshii, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/741,007

(22) PCT Filed: Oct. 28, 2008

(86) PCT No.: PCT/JP2008/069993
§ 371 (c)(1),
(2), (4) Date: Jul. 9, 2010

(87) PCT Pub. No.: WO2009/057798
PCT Pub. Date: May 7, 2009

(65) Prior Publication Data
US 2010/0317899 A1  Dec. 16, 2010

(30) Foreign Application Priority Data
Nov. 1, 2007  (JP) .................................. 2007-284855
Jul. 14, 2008  (JP) .................................. 2008-182398

(51) Int. Cl.
*C07C 409/06* (2006.01)
(52) U.S. Cl. ....................................... 568/569; 568/570
(58) Field of Classification Search ................. 568/569, 568/570
See application file for complete search history.

(56) References Cited

U.S. PATENT DOCUMENTS
2007/0167658 A1  7/2007  Onuma et al.

FOREIGN PATENT DOCUMENTS
JP  2001-11045 A  1/2001
JP  2001-270880 A  10/2001
JP  2005-97204 A  4/2005
JP  2007-217399 A  8/2007

OTHER PUBLICATIONS
International Search Report for International Application PCT/JP2008/069993, Dec. 22, 2008.

*Primary Examiner* — Sikarl Witherspoon
(74) *Attorney, Agent, or Firm* — Roberts Mlotkowski Safran & Cole, P.C.

(57) ABSTRACT

A process for producing an alkylbenzene hydroperoxide from an alkylbenzene solution containing 0.01 to 10 mmol/kg of phenols by subjecting the solution to oxidation with an oxygen-containing gas, including allowing a compound represented by formula (I) to be present in the alkylbenzene solution:

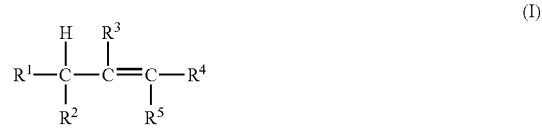

(I)

wherein $R^1$, $R^2$, $R^3$, $R^4$ and $R^5$ independently represent a hydrogen atom, an alkyl group or an aryl group and may combine with each other to form a non-aromatic ring, the molar ratio of the compound represented by formula (I) to the phenols in the alkylbenzene solution being 0.4 mol/mol or higher;

is advantageous in providing economical and high-yield production of an alkylbenzene hydroperoxide.

4 Claims, No Drawings

PROCESS FOR PRODUCING ALKYLBENZENE HYDROPEROXIDE

This application is a national stage of PCT/JP2008/069993, filed on Oct. 28, 2008, which claims priority to the following applications: Japanese Patent Application No. 2007-284855, filed on Nov. 1, 2007; and Japanese Patent Application No. 2008-182398, filed Jul. 14, 2008. Each of these documents is incorporated herein by reference in its entirety.

TECHNICAL FIELD

The present invention relates to a process for producing an alkylbenzene hydroperoxide. In more particular, the invention relates to a process for producing an alkylbenzene hydroperoxide from an alkylbenzene as a starting material by oxidizing the alkylbenzene with an oxygen-containing gas, which is advantageous in providing economical and high-yield production of an alkylbenzene hydroperoxide.

BACKGROUND ART

Processes are known which produce an alkylbenzene hydroperoxide from an alkylbenzene as a starting material by oxidizing the alkylbenzene with an oxygen-containing gas. However, it is known that phenols present in an alkylbenzene act as oxidation inhibitors, thereby impeding efficient progress of the oxidation reaction. Thus, to obtain a desired alkylbenzene hydroperoxide, such a problem has been usually dealt with by raising the reaction temperature or increasing the reaction time.

Several processes are described in Patent Document 1 in which the concentration of phenols in an alkylbenzene is decreased and the alkylbenzene with the decreased concentration of phenols is oxidized with an oxygen-containing gas. The processes, described in the above document, of decreasing the concentration of phenols are: to let phenols out from the system by distillation, alkali washing or the like; to convert phenols into some other compounds through an appropriate reaction; and to decrease the concentration of phenols using an adsorbent or the like. These processes, however, require additional equipment, such as a distillation column, a washing container, a reactor or an adsorption column, and are problematic in that they are not satisfactory from the viewpoint of economical and high-yield production of alkylbenzene hydroperoxides.

[Patent Document 1] JP 2001-270880 A

DISCLOSURE OF THE INVENTION

Problem to be Solved by the Invention

Under these conditions, an object of the present invention is to provide a process for producing an alkylbenzene hydroperoxide from an alkylbenzene as a starting material by oxidizing the alkylbenzene with an oxygen-containing gas, which is advantageous in providing economical and high-yield production of an alkylbenzene hydroperoxide.

Means for Solving the Problem

Specifically, the present invention relates to a process for producing an alkylbenzene hydroperoxide from an alkylbenzene solution containing 0.01 to 10 mmol/kg phenols by subjecting the solution to oxidation with an oxygen-containing gas, including allowing a compound represented by formula (I) to be present in the alkylbenzene solution:

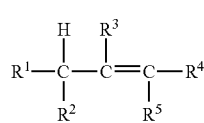

wherein $R^1$, $R^2$, $R^3$, $R^4$ and $R^5$ independently represent a hydrogen atom, an alkyl group or an aryl group and may combine with each other to form a non-aromatic ring, the molar ratio of the compound represented by formula (I) to the phenols in the alkylbenzene solution being 0.4 mol/mol or higher.

ADVANTAGEOUS EFFECT OF THE INVENTION

Thus, the present invention can provide a process for producing an alkylbenzene hydroperoxide from an alkylbenzene as a starting material by oxidizing the alkylbenzene with an oxygen-containing gas, which is advantageous in providing economical and high-yield production of an alkylbenzene hydroperoxide.

The alkylbenzene used in the present invention includes, for example, ethylbenzene, isopropylbenzene, sec-butylbenzene, isopropylmethylbenzene and diisopropylbenzene. It can be used each alone or in combination of two or more. The oxidation of alkylbenzenes is carried out by autoxidation using an oxygen-containing gas such as air or oxygen-enriched air. The oxidation may be carried out in the presence of an alkaline aqueous solution. Any alkaline aqueous solutions can be used. For example, fresh alkaline aqueous solutions, aqueous solutions recovered from those used in the oxidation process, or mixtures of an aqueous solution recovered from those used in the oxidation process and a fresh alkaline aqueous solution can be used. Examples of fresh alkaline aqueous solutions used include: solutions prepared by dissolving, in water, an alkaline metal compound such as NaOH and KOH; an alkaline earth metal compound; an alkaline metal carbonate such as $Na_2CO_3$ and $NaHCO_3$, ammonia, $(NH_4)_2CO_3$, or an alkaline metal ammonium carbonate. Any alkaline aqueous solutions recovered from those used in the oxidation process can be used; however, an aqueous phase is usually used which is obtained by separating a liquid phase obtained from the oxidation reactor into an oil phase and an aqueous phase. The reaction temperature usually ranges from 50 to 200° C. and the reaction pressure is generally between atmospheric pressure and 5 MPa.

The phenols contained in the alkylbenzene used in the present invention can be any phenols. Examples of such phenols include: phenol, dihydroxybenzene, and alkyl phenols such as cresol, ethylphenol, isopropylphenol and butylphenol.

The concentration of the phenols in the alkylbenzene used in the present invention can be 0.01 to 10 mmol/kg, preferably 0.1 to 5 mmol/kg. When the concentration of the phenols is too high, the yield of the alkylbenzene hydroperoxide is sometimes not satisfactorily high. When the concentration of the phenols is too low, a purification step of alkylbenzene becomes sometimes necessary, which would not be economical.

The alkylbenzene solutions used in the present invention, which contain 0.01 to 10 mmol/kg of phenols, include: for example, unreacted isopropylbenzene recovered in the process where isopropylbenzene hydroperoxide obtained by oxidizing isopropylbenzene with an oxygen-containing gas is brought into contact with an acid catalyst to obtain phenol and acetone. They also include: for example, unreacted ethylbenzene recovered in the process where ethylbenzene hydroperoxide obtained by oxidizing ethylbenzene with an oxygen-containing gas is reacted with propylene in the presence of an epoxidizing catalyst to obtain propylene oxide; and unreacted isopropylbenzene recovered in the process where isopropylbenzene hydroperoxide obtained by oxidizing isopropylbenzene with an oxygen-containing gas is reacted with propylene in the presence of an epoxidizing catalyst to obtain propylene oxide.

In the present invention, the process includes allowing a compound represented by formula (I) to be present in an alkylbenzene solution:

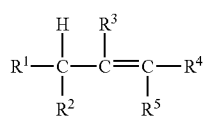
(I)

wherein $R^1$, $R^2$, $R^3$, $R^4$ and $R^5$ independently represent a hydrogen atom, an alkyl group or an aryl group and may combine with each other to form a non-aromatic ring.

The compounds used in the present invention, which are represented by formula (I), can be any compounds as long as they have the structure represented by formula (I). In the formula, $R^1$, $R^2$, $R^3$, $R^4$ and $R^5$ independently represent a hydrogen atom, an alkyl group or an aryl group and they, particularly any two of them, may combine with each other to form a non-aromatic ring.

Examples of the compounds used in the present invention, which are represented by formula (I), include: alkenes such as propylene, butene, pentene, 1-hexene, 2-hexene, cyclohexene, methylcyclohexene, ethylcyclohexene, ethenylcyclohexane, isopropylcyclohexene, isopropenylcyclohexane, diisopropylcyclohexene, diisopropenylcyclohexane, α-methylstyrene, β-methylstyrene, and diisopropenylbenzene.

The molar ratio of the compound represented by formula (I) to the phenols in the alkylbenzene solution according to the present invention should be 0.4 mol/mol or higher. It preferably ranges from 0.4 to 20 mol/mol. When the ratio is too low, the yield of the alkylbenzenehydroperoxide is sometimes not satisfactorily high due to strong oxidation inhibition. When the ratio is too high, the yield of the alkylbenzenehydroperoxide is sometimes not satisfactorily high due to the oxidation inhibition caused by the by-products from the compound represented by formula (I).

The concentration of the compound represented by formula (I) according to the present invention in an alkylbenzene solution is preferably 0.1 to 20 mmol/kg and more preferably 0.2 to 10 mmol/kg. If the concentration is too low, the oxidation may be inhibited greatly so that the alkylbenzene hydroperoxide cannot be sometimes obtained in satisfactorily high yield. If the concentration is too high, the yield of the alkylbenzenehydroperoxide is sometimes not satisfactorily high due to the oxidation inhibition caused by the by-product from the compound represented by formula (I).

Any processes, as long as they include allowing a compound represented by formula (I) to be present in an alkylbenzene solution that contains phenols, can be used as a process for obtaining an alkylbenzene solution containing a compound represented by formula (I) and used in the present invention. Examples of such processes include: adding a compound represented by formula (I) to an alkylbenzene solution containing phenols; and mixing an alkylbenzene solution that contains a compound represented by formula (I) with an alkylbenzene solution that contains phenols.

The alkylbenzene hydroperoxide obtained in the present invention can be used as a starting material for producing phenols and acetone. For example, isopropylbenzene hydroperoxide obtained is brought into contact with an acid catalyst to produce a mixture containing phenol and acetone, and the mixture is separated and purified into phenol and acetone. Examples of acid catalysts used include: sulfuric acid, perchloric acid, hydrochloric acid, hydrofluoric acid, phosphotungstic acid, phosphomolybdic acid, ion-exchange resins, and silica-alumina.

The alkylbenzene hydroperoxide obtained in the present invention can be used as a starting material for producing an alkylene oxide. For example, isopropylbenzene hydroperoxide obtained is reacted with propylene in the presence of a titanium-containing catalyst to produce a mixture of propyleneoxide and cumyl alcohol. After the mixture is separated, the obtained cumyl alcohol is reacted with hydrogen in the presence of hydrogenolysis catalyst to produce isopropylbenzene, and the isopropylbenzene is recycled as a starting material for the oxidation process. Further, the cumyl alcohol is converted into α-methylstyrene in the presence of dehydration catalyst, the α-methylstyrene is reacted with hydrogen in the presence of hydrogenation catalyst to produce isopropylbenzene, and the isopropylbenzene can be recycled as a starting material for the oxidation process. As another example, ethylbenzene hydroperoxide obtained is reacted with propylene in the presence of a titanium- or molybdenum-containing catalyst to produce a mixture of propylene oxide and 1-phenylethylalcohol. After the mixture is separated, the obtained 1-phenylethylalcohol is dehydrated in the presence of a dehydration catalyst to produce styrene.

EXAMPLES

The present invention will be described in more detail below based on several examples; however, it is not to be understood that these examples are intended to limit the present invention.

Example 1

A continuous flow reactor unit with a 1 L glass autoclave was used as a reactor. Into the reactor, 280 g of isopropylbenzene solution containing isopropylbenzene hydroperoxide (isopropylbenzene hydroperoxide: 9.0% by weight) and 7.0 g of aqueous solution containing sodium carbonate were charged. An isopropylbenzene solution containing o-isopropylphenol and 1-isopropyl-1-cyclohexene (o-isopropylphenol: 0.51 mmol/kg, 1-isopropyl-1-cyclohexene: 4.0 mmol/kg, 1-isopropyl-1-cyclohexene/o-isopropylphenol: 7.8 mol/mol), an aqueous solution containing sodium carbonate, and air were fed at feeding rates of 207 g/h, 6.0 g/h and 260 Nml/min, respectively, to the reactor. The resulting mixture in the reactor was subjected to 6.0 hours continuous flow reaction at 0.65 MPa-G and 120° C. The concentration of oxygen in the exhaust gas when the reaction was in the steady state was 3% by volume. And the analysis of the oil layer of the recovered solution, which was sampled 5 hours to 6 hours after the starting of the reaction, showed that the concentration of isopropylbenzene hydroperoxide in the oil phase was 9.6% by weight.

Example 2

The same procedure as in Example 1 was repeated except that an isopropylbenzene solution containing o-isopropylphenol and 1-isopropyl-1-cyclohexene (o-isopropylphenol: 0.55 mmol/kg, 1-isopropyl-1-cyclohexene: 0.48 mmol/kg, 1-isopropyl-1-cyclohexene/o-isopropylphenol: 0.9 mol/mol), an aqueous solution containing sodium carbonate, and air were fed to the reactor at feeding rates of 205 g/h, 6.3 g/h and 260 Nml/min, respectively, and subjected to 6.1 hours continuous flow reaction at 0.65 MPa-G and 119° C. The concentration of oxygen in the exhaust gas when the reaction was in the steady state was 3% by volume. And the analysis of the oil layer of the recovered solution, which was sampled 5 hours to 6.1 hours after the starting of the reaction, showed that the concentration of isopropylbenzene hydroperoxide in the oil phase was 8.5% by weight.

Example 3

The same procedure as in Example 1 was repeated except that an isopropylbenzene solution containing o-isopropylphenol and α-methylstyrene (o-isopropylphenol: 0.56 mmol/kg, α-methylstyrene: 4.5 mmol/kg, α-methylstyrene/o-isopropylphenol: 8.0 mol/mol), an aqueous solution containing sodium carbonate, and air were fed to the reactor at feeding rates of 206 g/h, 6.4 g/h and 260 Nml/min, respectively, and subjected to 6.0 hours continuous flow reaction at 0.65 MPa-G and 118° C. The concentration of oxygen in the exhaust gas when the reaction was in the steady state was 2% by volume. And the analysis of the oil layer of the recovered solution, which was sampled 5 hours to 6 hours after the starting of the reaction, showed that the concentration of isopropylbenzene hydroperoxide in the oil phase was 8.7% by weight.

Example 4

The same procedure as in Example 1 was repeated except that an isopropylbenzene solution containing o-isopropylphenol and α-methylstyrene (o-isopropylphenol: 0.51 mmol/kg, α-methylstyrene: 0.51 mmol/kg, α-methylstyrene/o-isopropylphenol: 1.0 mol/mol), an aqueous solution containing sodium carbonate, and air were fed to the reactor at feeding rates of 206 g/h, 6.4 g/h and 260 Nml/min, respectively, and subjected to 6.0 hours continuous flow reaction at 0.65 MPa-G and 119° C. The concentration of oxygen in the exhaust gas when the reaction was in the steady state was 2% by volume. And the analysis of the oil layer of the recovered solution, which was sampled 5 hours to 6 hours after the starting of the reaction, showed that the concentration of isopropylbenzene hydroperoxide in the oil phase was 8.5% by weight.

Comparative Example 1

The same procedure as in Example 1 was repeated except that an isopropylbenzene solution containing o-isopropylphenol and α-methylstyrene (o-isopropylphenol: 0.51 mmol/kg, α-methylstyrene: 0.17 mmol/kg, α-methylstyrene/o-isopropylphenol: 0.3 mol/mol), an aqueous solution containing sodium carbonate, and air were fed to the reactor at feeding rates of 213 g/h, 6.6 g/h and 260 Nml/min, respectively, and subjected to 5.5 hours continuous flow reaction at 0.65 MPa-G and 120° C. The concentration of oxygen in the exhaust gas when the reaction was in the steady state was 2% by volume. And the analysis of the oil layer of the recovered solution, which was sampled 4.5 hours to 5.5 hours after the starting of the reaction, showed that the concentration of isopropylbenzene hydroperoxide in the oil phase was 8.1% by weight.

Comparative Example 2

The same procedure as in Example 1 was repeated except that an isopropylbenzene solution containing o-isopropylphenol and α-methylstyrene (o-isopropylphenol: 0.51 mmol/kg, α-methylstyrene: 0.17 mmol/kg, α-methylstyrene/o-isopropylphenol: 0.3 mol/mol), an aqueous solution containing sodium carbonate, and air were fed to the reactor at feeding rates of 205 g/h, 6.8 g/h and 174 Nml/min, respectively, and subjected to 6.0 hours continuous flow reaction at 0.65 MPa-G and 119° C. The concentration of oxygen in the exhaust gas when the reaction was in the steady state was 2% by volume. And the analysis of the oil layer of the recovered solution, which was sampled 5.5 hours to 6.0 hours after the starting of the reaction, showed that the concentration of isopropylbenzene hydroperoxide in the oil phase was 6.2% by weight.

The invention claimed is:

1. A process for producing an alkylbenzene hydroperoxide from an alkylbenzene solution containing 0.01 to 10 mmol/kg of phenols by subjecting the solution to oxidation with an oxygen-containing gas, comprising allowing a compound represented by formula (I) to be present in the alkylbenzene solution:

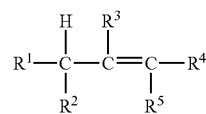

(I)

wherein $R^1$, $R^2$, $R^3$, $R^4$ and $R^5$ independently represent a hydrogen atom, an alkyl group or an aryl group and may combine with each other to form a non-aromatic ring, the molar ratio of the compound represented by formula (I) to the phenols in the alkylbenzene solution being 0.4 mol/mol or higher.

2. The process according to claim 1, wherein the alkylbenzene is isopropylbenzene and the alkylbenzene hydroperoxide is isopropylbenzene hydroperoxide.

3. The process according to claim 1, wherein the alkylbenzene is ethylbenzene and the alkylbenzene hydroperoxide is ethylbenzene hydroperoxide.

4. The process according to claim 1, wherein the alkylbenzene solution contains the compound represented by formula (I) in a concentration of from 0.1 to 20 mmol/kg.

* * * * *